US010561693B2

(12) United States Patent
Pertile et al.

(10) Patent No.: US 10,561,693 B2
(45) Date of Patent: Feb. 18, 2020

(54) CULTIVATION, PROCESSING, AND SYNTHESIS OF CANNABIDIOLS

(71) Applicant: MariJ Pharmaceuticals, Inc., Clearwater, FL (US)

(72) Inventors: Richard Pertile, Clearwater, FL (US); Travis Black, San Tan Valley, AZ (US)

(73) Assignee: MariJ Pharmaceuticals, Inc., Clearwater, FL (US)

( * ) Notice: Subject to any disclaimer, the term of this patent is extended or adjusted under 35 U.S.C. 154(b) by 0 days.

(21) Appl. No.: 16/115,900

(22) Filed: Aug. 29, 2018

(65) Prior Publication Data

US 2019/0134122 A1 May 9, 2019

Related U.S. Application Data

(60) Provisional application No. 62/553,335, filed on Sep. 1, 2017.

(51) Int. Cl.
| | |
|---|---|
| *A61K 36/185* | (2006.01) |
| *C07C 37/80* | (2006.01) |
| *A61K 31/047* | (2006.01) |
| *C07C 37/68* | (2006.01) |

(52) U.S. Cl.
CPC .......... *A61K 36/185* (2013.01); *A61K 31/047* (2013.01); *C07C 37/685* (2013.01); *C07C 37/80* (2013.01); *A61K 2236/15* (2013.01); *A61K 2236/37* (2013.01); *A61K 2236/39* (2013.01); *A61K 2236/55* (2013.01); *C07C 2601/16* (2017.05)

(58) Field of Classification Search
CPC .. A61K 36/185; A61K 31/045; A61K 31/047; A61K 2236/15; A61K 2236/37; A61K 2236/39; A61K 2236/35; C07C 37/685; C07C 37/80
See application file for complete search history.

(56) References Cited

U.S. PATENT DOCUMENTS

| | | | |
|---|---|---|---|
| 2,304,669 A | 12/1942 | Adams | |
| 6,403,126 B1* | 6/2002 | Webster | A61K 36/185 424/725 |
| 6,630,507 B1 | 10/2003 | Hampson | |
| 2003/0017216 A1* | 1/2003 | Schmidt | A61K 36/185 424/725 |
| 2004/0192760 A1* | 9/2004 | Whittle | A61K 9/0031 514/454 |
| 2006/0167283 A1* | 7/2006 | Flockhart | C07C 37/70 549/390 |
| 2016/0346339 A1* | 12/2016 | Finley | A61K 31/355 |
| 2018/0362429 A1* | 12/2018 | Zhang | C07C 37/685 |

FOREIGN PATENT DOCUMENTS

| | | | | |
|---|---|---|---|---|
| CN | 106278828 | * | 1/2017 | .......... C07C 37/685 |
| WO | WO 2016/153347 | * | 9/2016 | ............ C07C 37/70 |

* cited by examiner

*Primary Examiner* — Yate' K Cutliff
(74) *Attorney, Agent, or Firm* — Larson & Larson, P.A.; Justin P. Miller; Frank Liebenow

(57) ABSTRACT

The process described below is a method of making tinctures starting with extraction of a full spectrum oil from a biomass, then activating the cannabinoids in the full spectrum oil, finally formulating tinctures using the activated full spectrum oil.
Optional additional steps of winterization, distillation, and isolation increase the purity of the resulting product.

3 Claims, 1 Drawing Sheet

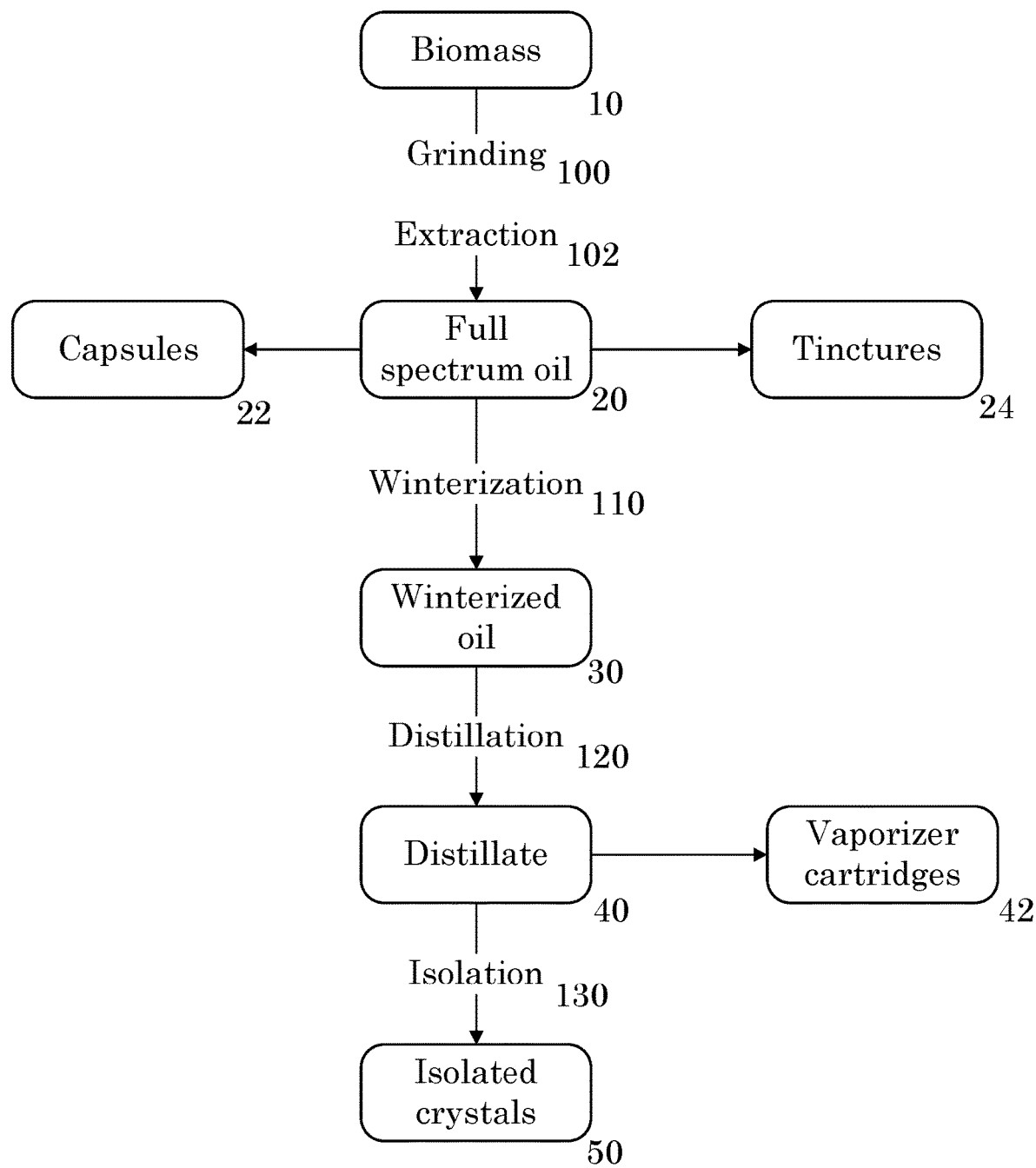

CULTIVATION, PROCESSING, AND SYNTHESIS OF CANNABIDIOLS

CROSS-REFERENCE TO RELATED APPLICATION

This application is a non-provisional application that claims priority to provision application Ser. No. 62/553,335, filed Sep. 1, 2017, titled Cultivation, Processing, and Synthesis of Cannabidiols.

FIELD

This invention relates to the field of extracting biological compounds from organic matter and more particularly to a process for extracting THC oil and CBD, or cannabinoid oil, from a biomass to create tinctures for medicinal uses.

BACKGROUND

Cannabinoids have recently become part of mainstream discussion.

A cannabinoid is a chemical compound, such as cannabinol, THC, or cannabidiol.

Cannabinoids include compounds such as THC that have high affinity for the cannabinoid receptor and compounds that do not have significant affinity for the cannabinoid receptor, such as CBD.

As medical marijuana is being legalized in more and more states, the medical research surrounding marijuana and cannabinoids is increasing rapidly. One such cannabinoid that has shown the potential for multiple medical uses is cannabidiol (CBD).

CBD is the second most abundant cannabinoid found in marijuana. Unlike its counterpart, tetrahydrocannabinol (THC), CBD is non-psychoactive.

Various studies have been performed on CBD. CBD has various medical uses but the psychoactive nature of THC still presents a major hurdle to using marijuana in its natural form to treat those diseases. As such, it is important to find new ways of acquiring CBD for both medicinal uses and research.

Some examples of diseases and disorders for which cannabinoids have shown promising early results include: cancer, arthritis, epilepsy, Huntington's disease, nausea, diabetes, and irritable bowel syndrome. Thus, cannabinoids have the ability to be used for the treatment of multiple ailments without many of the negative side effects that are associated with current pharmaceuticals.

What is needed is a tincture of full spectrum hemp extract that can be used to treat various ailments while minimizing or eliminating the psychoactive effects.

SUMMARY

The process described below is a method of making tinctures starting with extraction of a full spectrum oil from a biomass, then activating the cannabinoids in the full spectrum oil, finally formulating tinctures using the activated full spectrum oil.

There are multiple options regarding what type, and which portions, of *Cannabis* may form the biomass. While there is disagreement regarding the exact number of species of *Cannabis*, there are commonly thought that there are three. *Cannabis Sativa* is the most common species. It is tall, and found primary in warm regions. *Cannabis* Indica is a shorter plant with a bushy appearance found in cooler climates. *Cannabis Ruderalis* is the informal name for short, wild varieties found in Asia and Europe.

Within the above species, different varieties exist that have been cultivated for specific characteristics. For example, some varieties are bred for high THC content, or low THC content. Similarly, some are bred for a high or low CBD content.

The preferred biomass is industrial hemp. Industrial hemp is preferred because the THC levels are lower and CBD levels are higher.

The entire plant is used, including stems, leaves, and flowers.

To begin the process, a full spectrum oil is extracted from the biomass. The full spectrum oil contains all of the cannabinoids present in the biomass, in addition to other fatty materials and plant waste.

After extraction, the full spectrum oil is heated to activate the cannabinoids. Heating decarboxylates the cannabinoids—decarboxylated cannabinoids are referred to as "activated." "Activating" is the conversion of all acidic cannabinoids such as CBDA and THCA, among others, to their non-acidic "active" versions. The difference between acidic and non-acidic is the presence of a carboxylic acid function group, or COOH group. Activation is caused by a chemical reaction called decarboxylation. Decarboxylation removes this function group and releases $CO_2$. The quantity of decarboxylation is a function of heat applied over time elapsed. The resulting activated oil is then used to create a tincture.

Optionally, after activating, the full spectrum oil may be further processed through winterization, distillation, and then isolation to obtain a pure CBD oil. The resulting pure CBD oil contains no THC and thus has no psychoactive effects.

BRIEF DESCRIPTION OF THE DRAWINGS

The invention can be best understood by those having ordinary skill in the art by reference to the following detailed description when considered in conjunction with the accompanying drawings in which:

FIG. 1 illustrates a flowchart of the process of processing biomass to separate and isolate CBD.

DETAILED DESCRIPTION

Grinding and Extraction

The first step is preparation of the raw material. Specifically, *cannabis* biomass 10, or industrial hemp, sourced from a supplier. The biomass 10 includes whole *cannabis* flowers and stems.

Preparation starts with grinding 100. The preferred grinder is a Hobart HCM450 45-quart vertical cutter and mixer with five horsepower motor.

The grinding 100 continues until no particle is larger than a pea. The goal of grinding is to increase the surface area of the resulting material, which results in a more efficient extraction of oils.

The resulting ground material is divided into 10-pound quantities in preparation for extraction.

The second step is extraction 102, where live resin is removed from the biomass. The live resin is a concentrated oil containing cannabinoids. The cannabinoids are extracted from the ground plant matter using supercritical fluid extraction.

Supercritical fluid extraction uses a supercritical fluid to dissolve and extract oils from a mass of solid material. A supercritical fluid is a substance at a temperature and pressure above its critical point. The critical point is a temperature and pressure point above which there is no distinct liquid or gas phase of a material. Critical points vary for different materials. By forcing the fluid to a state above its critical point, the substance takes on the properties of both a liquid and a gas. Carbon dioxide is used as the supercritical fluid.

Extraction includes the following steps:
Placing the ground material into the vessel or chamber of a supercritical fluid extractor;
The chamber is connected to a source of supercritical fluid and a pressurizing pump;
The vent is closed;
The pump is activated, and the pressure in the chamber is allowed to rise to a setpoint, at which the pump is deactivated;
The chamber is optionally heated;
After being permitted to soak, the pump is reactivated, and the drain and vent are opened enough to permit oil and supercritical fluid to exit, but left closed sufficiently to maintain pressure in the chamber;
A catch container collects a mix of solid supercritical fluid and extracted oil;
The extraction process is allowed to continue until the desired percentage of oil is extracted;
The solids of the supercritical fluid are allowed to evaporate, leaving behind the extracted oil.

Approximately 65-70 pounds of $CO_2$ liquid is required to complete the oil extraction from 10 pounds of plant material.

Optimal extraction occurs at 35 degrees Celsius, 95 degrees Fahrenheit, at a pressure of 1,850 PSI. This pressure is held for four hours, and then dropped by 250-300 PSI every forty-five minutes until atmospheric pressure is reached.

After supercritical extraction has removed all of the cannabinoids from the biomass, the resulting product is a resin with the texture of cake frosting. The resin contains cannabinoids, chlorophyll, plant waxes, and plant fats.

To convert the resin into an oil, the carbon dioxide must be removed, or purged.

Purging carbon dioxide is performed by slowly heating and stirring the resin until the carbon dioxide has left the mixture. The preferred method is to:
Fill a flask is filled with the extracted resin;
Heat the resin to 240 degrees Fahrenheit;
Stir the resin while it continues to heat;
Continue stirring, and maintain temperature, so long as bubbles continue to rise to the surface—these bubbles are $CO_2$ that is leaving solution;
When the bubbles stop, the resulting oil is permitted to cool.

Once purging is complete, the activated full spectrum oil 20 contains activated cannabinoids, chlorophyll, plant waxes, and plant fats.

Post-Extraction Concentration Measurement

Following extraction, the concentration of the resulting full spectrum oil 20 is measured to determine the dilution ratios for subsequent steps.

First, the density of the full spectrum oil 20 is measured.

Second, a liquid chromatography machine is used to measure the cannabinoids present in the full spectrum oil. An example machine is the Flexar from Perkin Elmer.

The resulting report is associated with the tested batch of full spectrum oil 20, and used to calculate dilution ratios in subsequent steps.

With the concentration known, the full spectrum oil 20 may be used to form capsules, tinctures, or further processed through winterizing.

Capsules

To form a capsule 22, the desire ingredients are measured, mixed and heated. The resulting mixture is placed into capsules using a syringe.

Tincture

To form a tincture 24, the full spectrum oil is homogenized into a carrier oil. The preferred carrier oil is a medium chain triglyceride (MCT) oil derived from coconut oil ("carrier oil"). However, the carrier oil may be derived from other oils such as canola or avocado.

The ratio of carrier oil with to full spectrum oil is calculated based on the concentration measurement performed above, and the desired concentration of the resulting mixture.

The full spectrum oil and carrier oil are mixed in a vessel. Heat is applied while mixing to ensure a uniform mixture.

After the mixture has been homogenized, the tincture 24 is allowed to cool.

Once cool the mixture is cool, the tincture bottles can be filled. The amount of each of these substances added depends on the final bottle size and concentration desired. The preferred concentration is 20 mg/mL in a 30 mL bottle. At a concentration of 20 mg/mL in a 30 mL bottle, the total is mass of CBD is 600 mg per bottle.

Part of determining the proper formulation is obtaining the specific gravity of the carrier oil.

| Contents of one 1 oz. bottle | |
| --- | --- |
| Amount per bottle | 30 mL |
| Total mass CBD per bottle | 600 mg |
| THO/CBO | Depends on CBD concentration |
| Carrier oil | Depends on concentration of CBD rich oil as well as carrier specific gravity. |
| Total bottle | 30 mL |
| Concentration | 20 mg/mL |

Finally, the tincture is optionally sent to a third-party for verification of CBD concentration.

Winterize/De-Wax

As an alternative to preparing capsules or tinctures from the full spectrum oil, it may instead be further processed by winterizing.

Winterization 110 is the process of separating the plant substances from cannabinoids to produce a cannabinoid oil.

To winterize, first the full-spectrum oil 20 is mixed with ethanol. In the preferred embodiment, three parts ethanol are mixed with one part activated full-spectrum oil 20. After the activated full spectrum oil 20 and ethanol are mixed, the mixture is gently heated until the ethanol has evaporated. After excess ethanol has evaporated, the resulting mixture is stored at 0 degrees Celsius, or below, for between 24 hours and 48 hours. At temperatures below 0 degrees Celsius, fatty and waxy materials precipitate from the full-spectrum oil, falling to the bottom of the container. Following freezing, the mixture is filtered, the filter catching the precipitated ethanol and waxes.

The extraction and refinement steps are optionally repeated multiple times, until a winterized oil 30 of the desired clarity is obtained.

If the mixture is discolored, activated charcoal and diatomaceous earth may be added to remove impurities.

The resulting winterized oil 30 is clear and contains only cannabinoids, the plant waxes, plant fats, and chlorophyll having been filtered out The winterized oil 30 is now ready for distillation 120. Optionally, the winterized oil 30 can be stored and distilled in the future.

Distillation

To perform distillation 120, the winterized mixture is first placed in an evaporation flask. Next, a heating mantle is used to raise the temperature of the mixture to 100 degrees Celsius, or 212 degrees Fahrenheit. A vacuum pump is used to draw a vacuum, preferably between −8 to −10 mmHg.

When the vacuum pressure holds steady for five minutes, a second flask may be substituted and the operation repeated.

Note that the ideal vacuum pressure will vary depending on specific gravity of the oil and altitude at which the operation is performed.

Now, the temperature can be increased to 150 degrees Celsius, or 302 degrees Fahrenheit. At this temperature, the supercritical fluid has evaporated and the cannabinoids begin to evaporate from the winterized oil. The distillate containing the evaporated cannabinoids is collected and stored until ready for isolation.

Following distillation, the resulting distillate 40 may be used in devices such as vaporizer cartridges 42.

Optionally the CBD may be isolated from the distillate 40.

Isolation

Isolation 130 separates the cannabidiol from the distillate 40, thereby removing any other cannabinoids present.

To isolate the cannabidiol, first pour 200 mL of a non-polar solvent with two to five carbons into a flask. In the preferred embodiment, pentane is used as the solvent.

The mixture is then stirred and heated to 40 degrees Celsius, 104 degrees Fahrenheit. The distillate is slowly added to the solvent until the flask is full. Adding the maximum amount of distillate will create a supersaturated solution of cannabinoids in the solvent.

After the distillate has completely dissolved, the heat is removed. The flask is moved to a stable surface. The flask is allowed to sit for at least two days and up to one week. During this time, the pentane will evaporate with the solutes and other cannabinoids. Cannabidiol will slowly crystallize on the bottom of the flask.

After all of the pentane has evaporated, the remaining crystals at the bottom will be a CBD isolate having none of the psychoactive cannabinoids originally found in the biomass.

In some embodiments, the isolated crystals 50 are re-dissolved in pentane, then the pentane evaporates over a period of a few days to one week. This final step ensures the removal of all THC is left in the isolate.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes Cultivation, Processing, and Synthesis of Cannabidiols The process described below is a method of making tinctures starting with extraction of a full spectrum oil from a biomass, then activating the cannabinoids in the full spectrum oil, finally formulating tinctures using the activated full spectrum oil.

Optional additional steps of winterization, distillation, and isolation increase the purity of the resulting product.

What is claimed is:

1. A process for the removal of cannabidiols from industrial hemp comprising the steps of:
    grinding the industrial hemp, resulting in ground industrial hemp;
    extracting cannabinoids from the ground industrial hemp comprising the steps of:
        placing the ground industrial hemp into a chamber of a supercritical fluid extractor;
        pumping liquid $CO_2$ into the chamber, the liquid $CO_2$ becoming a supercritical fluid within the chamber, thereby pressurizing the chamber;
        allowing the mixture of supercritical fluid and ground industrial hemp to soak for a period of time;
        opening a drain to allow the supercritical fluid to pass into a vessel, the supercritical fluid now containing extracted oil;
        allowing the supercritical fluid to evaporate, leaving behind the extracted oil in the form of a resin;
    purging the resin of carbon dioxide comprising the steps of:
        filling a flask with the resin;
        heating the resin to 240 degrees Fahrenheit;
        stirring the resin until no bubbles of supercritical fluid rise to the surface of the resin;
        allowing the resin to cool, resulting in a full-spectrum oil;
    winterizing the full spectrum oil comprising the steps of:
        mixing the full-spectrum oil with ethanol at a ratio of one part full-spectrum oil to three parts ethanol to create an oil-ethanol mixture;
        heating the oil-ethanol mixture to evaporate the excess ethanol;
        cooling the oil-ethanol mixture to 32 degrees Fahrenheit or below and holding for between 24 and 48 hours, during which time fatty and waxy materials precipitate out of the full-spectrum oil;
        filtering the oil-ethanol mixture to remove the precipitated fatty and waxy materials, resulting in a winterized oil;
        adding activated charcoal and diatomaceous earth to the winterized oil to improve clarity;
    distilling the winterized oil comprising the steps of:
        heating the winterized oil to a temperature of 212 degrees Fahrenheit;
        applying a vacuum to the winterized oil of between minus 8 to minus 10 mmHg;
        increasing the temperature of the winterized oil to 302 degrees Fahrenheit, at which point the cannabinoids evaporate;
        collecting the evaporated cannabinoids, or distillate.

2. The method of claim 1, further comprising the steps of:
    isolating cannabidiols from the distillate comprising the steps of:
        heating 200 mL of a non-polar solvent with two to five carbons within a vessel to a temperature of 104 degrees Fahrenheit;

pouring remaining distillate into the vessel;
allowing the distillate to fully dissolve into the non-polar solvent;
allowing the vessel to rest uncovered, permitting the non-polar solvent and non-cannabidiol cannabinoids to evaporate.

3. The method of claim 1, wherein the supercritical fluid is carbon dioxide.

* * * * *